United States Patent [19]

Yuan

[11] Patent Number: 5,689,058
[45] Date of Patent: Nov. 18, 1997

[54] FRICTION MATERIAL EVALUATION APPARATUS

[75] Inventor: Yongbin Yuan, Winchester, Va.

[73] Assignee: Cooper Industries, Inc., Houston, Tex.

[21] Appl. No.: 771,022

[22] Filed: Dec. 20, 1996

[51] Int. Cl.$^6$ .................................................. G01N 19/02
[52] U.S. Cl. .................................................. 73/9
[58] Field of Search .................................................. 73/9, 10

[56] References Cited

U.S. PATENT DOCUMENTS

| | | |
|---|---|---|
| 2,887,874 | 5/1959 | Mason .................................................. 73/9 |
| 3,059,464 | 10/1962 | Deane .................................................. 73/9 |
| 3,269,003 | 8/1966 | Hollander et al. .................................................. 73/9 |
| 5,315,860 | 5/1994 | Dreilich et al. .................................................. 73/9 |

*Primary Examiner*—Robert Raevis
*Attorney, Agent, or Firm*—Thomas S. Baker, Jr.

[57] ABSTRACT

Evaluation apparatus for detecting the onset parameters of friction, wear and groan and squeal noise characteristics associated with a specimen of a particular brake friction material composition is provided with a movable apparatus table which carries both a variable-speed electric motor that drives a brake rotor and that has a near-zero speed capability and a reversible electric motor that may be selectively and independently actuated to advance the brake rotor into friction contact with a friction material specimen and with a normal-force that correlates to the output torque of the reversible electric motor.

2 Claims, 3 Drawing Sheets

5,689,058

FRICTION MATERIAL EVALUATION APPARATUS

FIELD OF THE INVENTION

This invention relates generally to evaluating friction materials such as those friction materials typically incorporated into automotive vehicle brake systems, and particularly concerns apparatus that may be advantageously utilized to determine the friction, wear, groan and squeal noise characteristics associated with different brake friction material compositions.

BACKGROUND OF THE INVENTION

Certain known machines for evaluating braking system friction materials are operated at fixed rotational speeds, and accordingly are not useful for determining the stick/slip characteristics associated with brake creep groan or measuring the relationship between the kinetic friction and the relative slide speed characteristic (μ-v curve) associated with squeal noise. Other known friction material evaluation machines such as inertia-type brake dynamometers have been utilized for testing braking system friction materials, and although capable of being operated at different or variable rotational speeds such are incapable of operating at near-zero rotational speeds and hence cannot be used to determine friction material stick/slip characteristics. Also, the prevalence of heavy mechanical components in the inertia-type brake dynamometer machines causes such machines to not be suited to the accurate measurement of the dynamic variation of sensed friction forces.

Examples of typical or representative prior art apparatus for testing brake materials for their various properties are disclosed in detail in U.S. Pat. No. 3,648,511 issued in the names of Groat, et al., U.S. Pat. No. 3,717,025 granted to Kronenberg, et al. and U.S. Pat. No. 5,315,860 granted to Dreilich, et al.

The friction material evaluation apparatus of the instant invention is capable of developing continuously variable friction surface relative speeds in the range of from 0 to approximately 110 miles per hour, for example, concurrent friction material contact pressure in the range of from 0 to approximately 1,000 pounds per square inch, for example, and controlled heating of the test friction surfaces to a temperature in the range of approximately from 69 F. to 1,000 F., for example, such as are necessary for advantageously determining not only brake friction and wear, but also μ-v curves and stick/slip characteristics, each for a wide spectrum of different brake friction material compositions.

SUMMARY OF THE INVENTION

The evaluation apparatus of the present invention is basically comprised of a base carrying one or more attached support rails for co-operation with a movable table, a variable-speed electric motor fixedly mounted on the movable table and rotationally connected to a brake rotor, a reversible electric motor also fixedly mounted on the sliding table and having a ball screw element which co-operates with a nut element fixedly attached to the base/rail combination, and a fixed tri-axis force sensor with a holder for mounting the friction material composition specimen that is to be evaluated for friction, wear and inherent noise characteristics. The apparatus also includes controls for operating the variable-speed electric motor and connected brake rotor element, at different rotational speeds, and for operating the reversible electric motor independently to change the position of the movable table and consequently the magnitude of the force pressing the rotating rotor element against the fixed test specimen and co-operating force sensor.

Further, the apparatus also includes a heater element and control for heating the brake rotor element at its specimen contact surface to a desired temperature that is controlled to a pre-selected temperature level that may be significantly elevated relative with respect to ambient temperature.

Optionally, the apparatus further may be constructed to be computer-controlled and with graphic displays for automatically and interactively executing desired evaluation procedures within the machine's capability limits, including changing specimen contact pressure, changing brake rotor rotational speed profiles, changing controlled temperatures, and recording the normal contact force which may include friction force on the specimen, instantaneous rotor speed and rotor surface temperature.

Other objects and advantages of the present invention will become apparent during consideration of the drawings, detailed description, and claims which follows.

DETAILED DESCRIPTION

Figure 1:
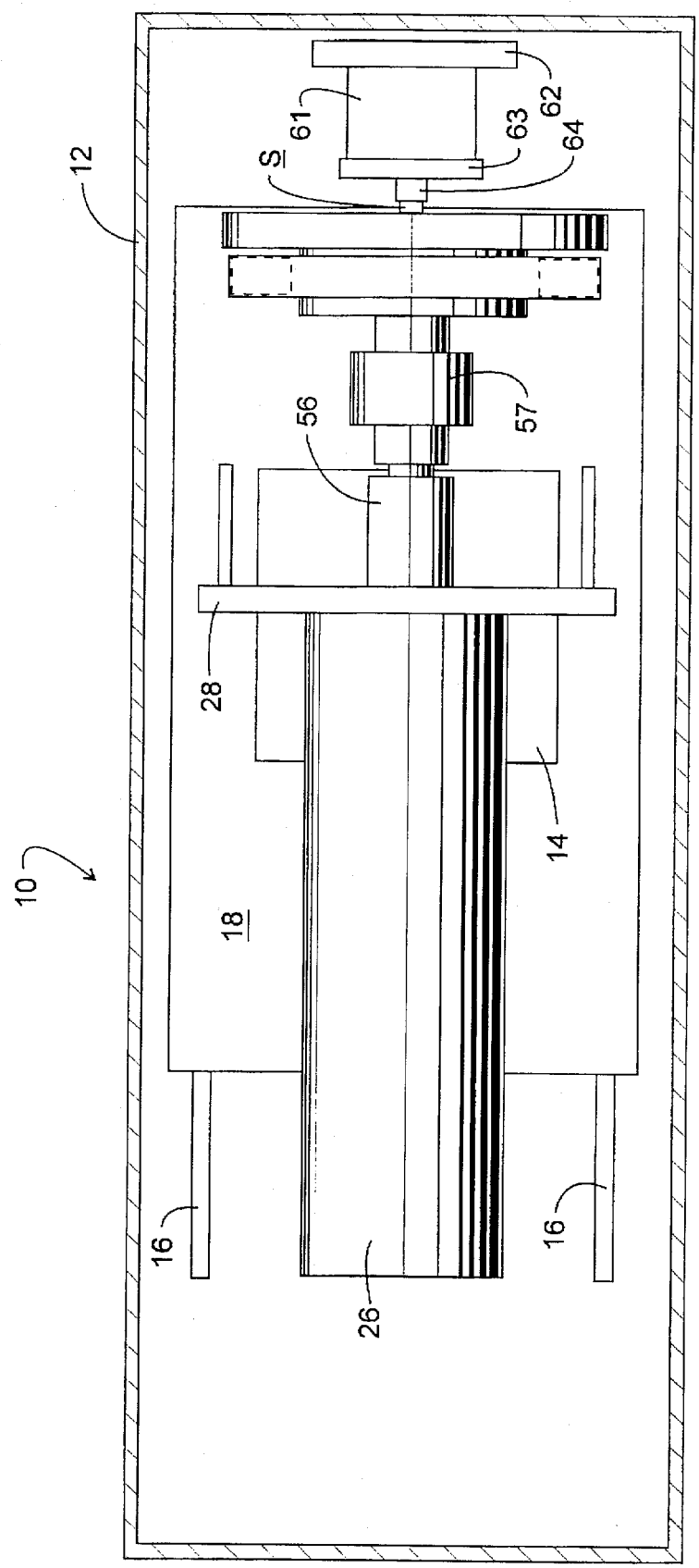
FIG. 1 is a schematic plan view of a preferred embodiment of the evaluation apparatus of the present invention.

A preferred embodiment of the evaluation test apparatus of the present invention is referenced generally as 10 in the drawings, is contained within a housing or support cabinet 12 having an accessible interior, and includes a base element 14, a pair of spaced-apart and parallel support rails 16 that are secured to base element 14, and a table 18 that has attached slide blocks 20 that slidably co-operate with support rails 16. Apparatus 10 further includes a conventional reversible electric table drive motor 22 that is mounted on a bracket 24 attached to table 18 and a conventional variable-speed electric rotor drive motor 26 that is mounted on a generally upright frame element 28 attached to table 18.

Table drive motor 22 has its output shaft 30 connected to one end of a ball screw drive element 32 by the conventional shaft coupling 34. Ball screw drive 32 in turn is supported at its opposite end by bearing block 36 that is secured to a bearing support 38 and that in turn is fixedly attached to and carried by table 18. Further, ball screw drive 32 is supported by a conventional bearing block 40 that co-operates with a nut element 42 that is fixedly joined to a support block 44 that passes through an interior opening 46 in table 18 and is rigidly joined to base element 14. Thus, rotation of the output shaft 30 of drive motor 22 and connected ball screw drive element 32 in either of their opposite rotational directions causes table 18 and all components supported thereon to be moved relative to nut 42 and base 14 in corresponding opposite linear directions, and selectively into and out of engagement with the friction material specimens being evaluated in apparatus 10 for its friction, wear and noisegenerating characteristics.

Variable speed electric rotor drive motor 26 has an output shaft, not shown, connected to an input shaft 54 of a brake rotor subassembly 52 via a conventional shaft coupling 56. The brake rotor subassembly shaft 52 is rotationally supported by bearing assembly 57 mounted on bearing support 38. Although not shown in the drawings, apparatus 10 includes a conventional tachometer device whose electrical energy voltage output is proportional to the rotational speed of rotor subassembly 52 and is utilized in connection with the determination and apparatus control by a computer assembly 59 of the sliding speed of a friction surface 58 of rotor subassembly 52 relative to a friction material specimen being evaluated. An electrical resistance or induction heater 60 secured to and supported by table element 18, and is positioned in surrounding relation to the hub of rotor subassembly 52. Also, and although not shown in the drawings, apparatus 10 preferably includes a non-contact type temperature sensor such as a conventional infra-red pyrometer which detects or senses the rotor surface temperature to which friction surface 58 of rotor subassembly 52 has been heated by resistance heater element 60 for both temperature-indication and temperature-control purposes.

Apparatus 10 further includes a conventional, high-sensitivity and high-accuracy force transducer 61 which is carried and supported in a fixed position by bracket 62 attached to base 14. Transducer 61 is preferably a conventional multi-axis type force sensor of which usually only two channels are utilized. A friction material specimen holder 64 is mounted on the force-sensitive face 63 of force transducer 61 and carries a readily-insertable and readily-withdrawable friction material specimen S.

Figure 2:
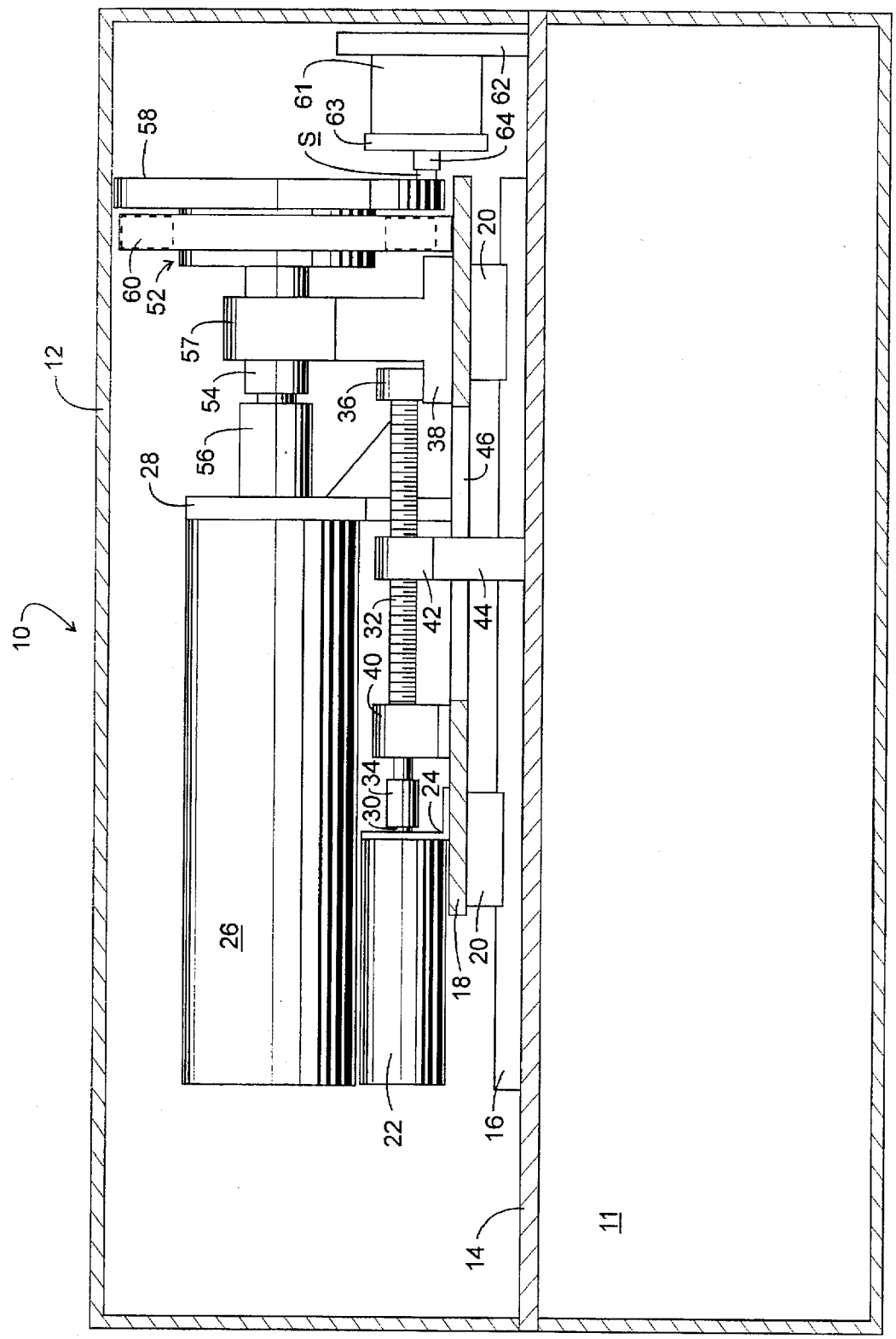
FIG. 2 is an elevation view of the FIG. 1 apparatus.
Figure 3:
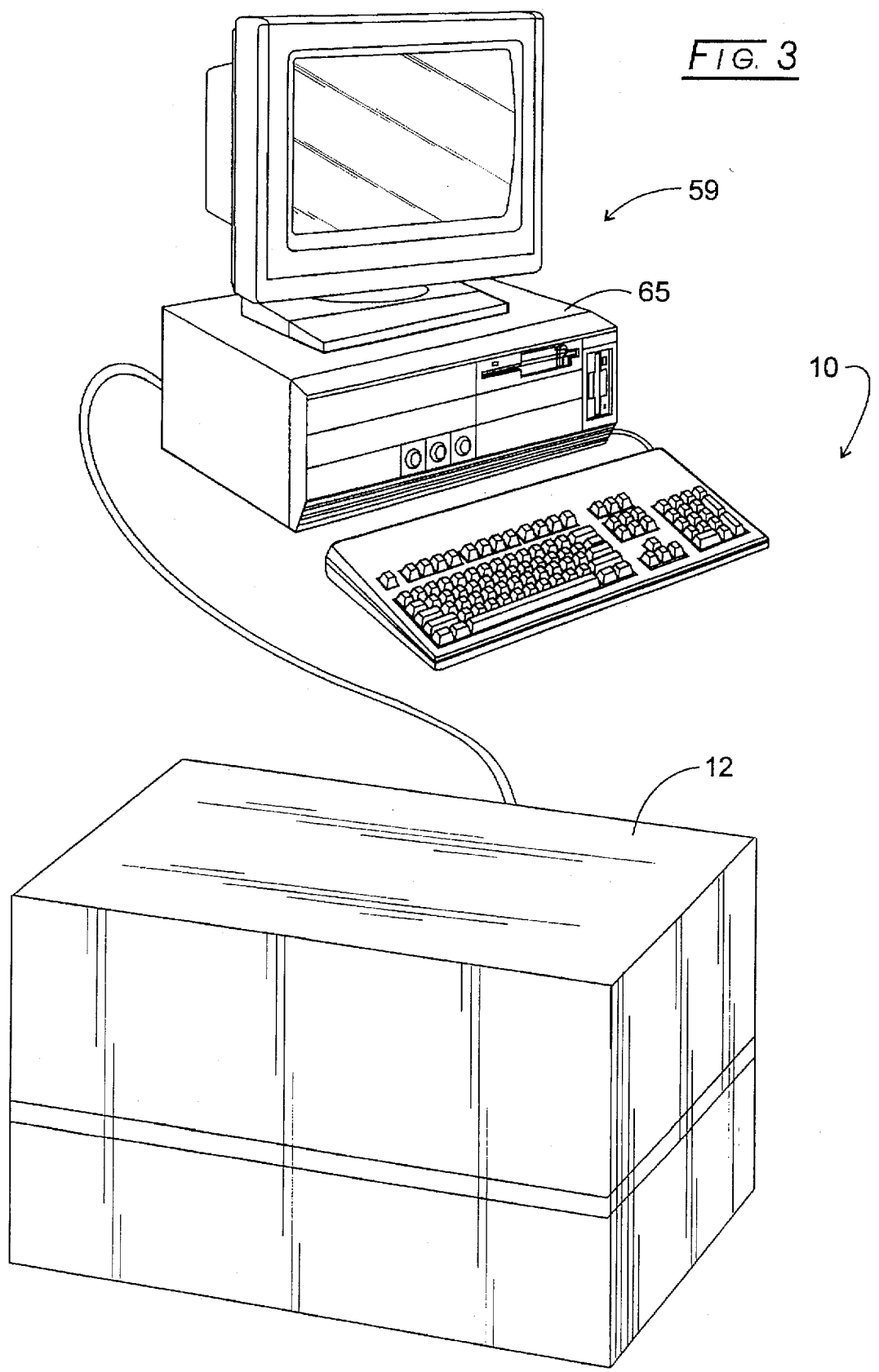
FIG. 3 is a perspective view showing a computer control attached to the evaluating apparatus of the subject invention.

In operation, apparatus 10 is placed in an initial condition wherein table element is moved leftward (FIG. 2) by reverse operation of table drive motor 22 to separate rotor subassembly friction surface 58 from specimen holder 64 a sufficient distance to permit the proper manual placement of friction material specimen S in holder 64. Rotor drive motor 26 is then energized to cause rotor subassembly 52 to rotate at the desired rotational speed. Table drive motor 22 may then be operated in an opposite direction to cause rotor friction surface 58 to contact friction material specimen S. The contact pressure between the specimen/holder combination S,64 may be varied or adjusted by changing the output torque of table drive motor 22. An interior space 11 is provided within housing 12 for the containment of the conventional electrical/electronic components and circuits for the operation and control of apparatus 10.

A conventional computer and monitor apparatus 65 with an internal data-acquisition card is used to present a graphical interface for the user of apparatus 10 to change and otherwise control friction contact pressure, rotor speed profile, normal contact force, friction force, instantaneous rotor speed and rotor surface temperature. The computer and monitor apparatus 65 may also be readily adapted to permit the definition and automatic execution of preferred friction material evaluation procedures through appropriate process parameter control.

Various changes may be made in the sizes, shapes, and materials of construction of the components which comprise my invention without departing from the scope or meaning of the claims which follow.

I claim as my invention:

1. Evaluation apparatus for use in determining the friction, wear, groan and squeal noise characteristics of a brake friction material, and comprising:

an apparatus base;

an apparatus movable table slidably supported on said apparatus base;

a force transducer fixedly positioned with respect to said apparatus base and having an attached friction material specimen holder;

a variable-speed electric motor supported by and fixedly positioned with respect to said apparatus movable table;

a brake rotor rotationally coupled to said variable-speed electric motor and having a friction surface that is spaced-apart from the friction material specimen holder attached to said force transducer and that selectively contacts a friction material specimen carried by and projecting from the friction material specimen holder attached to said force transducer;

a reversible electric motor fixedly positioned on said apparatus movable table;

ball screw and nut drive means co-operably connected to said reversible electric motor, to said apparatus movable table, and to said apparatus base; and control means for selectively varying the rotational speed of said variable-speed electric motor and the direction and magnitude of the output torque of said reversible electric motor until a specified contact load and relative slide speed are developed by the operating contact of the friction surface of said brake rotor with a friction material specimen carried by the friction material specimen holder attached to said force transducer, said variable-speed electric motor having a near-zero constant rotational operating speed capability, and said reversible electric motor operating independently of said variable-speed electric motor to advance said apparatus table through said ball screw drive means into selective engagement of the friction surface of said brake rotor element with a friction material specimen positioned in the friction material specimen holder attached to said force transducer and with a variable normal force that correlates to the output torque of said reversible electric motor.

2. The evaluation apparatus defined by claim 1 and further comprised of an electric heater element positioned in heating relation to said brake rotor, and of additional control means for selectively operating said electric heater element, said additional control means operating to selectively heat said brake rotor independently of the heat induced therein by frictional contact between the friction surface of said brake rotor with a friction material specimen carried by and projecting from the friction material specimen holder attached to said force transducer.

* * * * *